United States Patent
Lai et al.

(10) Patent No.: US 7,276,544 B2
(45) Date of Patent: Oct. 2, 2007

(54) PROCESS FOR MANUFACTURING INTRAOCULAR LENSES WITH BLUE LIGHT ABSORPTION CHARACTERISTICS

(75) Inventors: Yu-Chin Lai, Pittsford, NY (US); Dominic V. Ruscio, Webster, NY (US); George F. Green, Victor, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 235 days.

(21) Appl. No.: 10/657,356

(22) Filed: Sep. 8, 2003

(65) Prior Publication Data

US 2005/0055090 A1    Mar. 10, 2005

(51) Int. Cl.
*C08F 2/46*     (2006.01)
*G02C 7/04*     (2006.01)

(52) U.S. Cl. .................... 522/99; 522/104; 522/107; 522/150; 522/154; 522/148; 522/172; 522/182; 522/120; 522/16; 522/18; 522/20; 522/22; 522/29; 522/36; 522/37; 522/40; 522/50; 522/66; 522/74; 522/75; 522/71; 523/106; 523/107; 523/108; 351/159; 351/160; 351/160 R; 351/163

(58) Field of Classification Search .................. 522/99, 522/104, 107, 150, 154, 148, 172, 182, 16, 522/18, 20, 22, 29, 36, 37, 49, 50, 66, 120, 522/71, 74, 75; 523/106, 107, 108; 623/159, 623/160 R, 163
See application file for complete search history.

(56) References Cited

U.S. PATENT DOCUMENTS

| | | | |
|---|---|---|---|
| 4,304,895 A | 12/1981 | Loshaek | |
| 4,528,311 A | 7/1985 | Beard et al. | |
| 5,470,932 A | 11/1995 | Jinkerson | 526/312 |
| 5,528,322 A | 6/1996 | Jinkerson | 351/163 |
| 5,543,504 A | 8/1996 | Jinkerson | 534/856 |
| 5,662,707 A | 9/1997 | Jinkerson | 623/6 |
| 5,891,931 A | 4/1999 | Leboeuf et al. | 522/64 |
| 6,015,842 A | 1/2000 | LeBoeuf et al. | 522/64 |
| 6,353,069 B1 | 3/2002 | Freeman et al. | 526/319 |
| 6,632,887 B2 * | 10/2003 | LeBoeuf et al. | 525/203 |
| 6,632,905 B2 * | 10/2003 | Leboeuf | 526/303.1 |
| 2001/0014704 A1 | 8/2001 | Lai | |

FOREIGN PATENT DOCUMENTS

JP    2000-89171    3/2000

OTHER PUBLICATIONS

PCT/US2004/026776, "International Preliminary Report on Patentability," (Dec. 5, 2005).

* cited by examiner

*Primary Examiner*—Sanza L. McClendon

(57) ABSTRACT

A process for producing intraocular lenses (IOLs) capable of absorbing blue light and ultraviolet light using photo curing. Intraocular lenses so produced block blue light and ultraviolet light from reaching the retina of an eye implanted with the IOL. By blocking blue light and ultraviolet light from reaching the retina, the IOL thereby prevents potential damage to the retina.

18 Claims, 1 Drawing Sheet

PROCESS FOR MANUFACTURING INTRAOCULAR LENSES WITH BLUE LIGHT ABSORPTION CHARACTERISTICS

FIELD OF THE INVENTION

The present invention relates to a process for manufacturing intraocular lenses with blue light absorption characteristics. More particularly, the present invention relates to a process for manufacturing intraocular lenses using in a lens material one or more visible light photointiators having suitable absorption above 500 nm to cure the lens material using a visible light source.

BACKGROUND OF THE INVENTION

Since the 1940's optical devices in the form of intraocular lens (IOL) implants have been utilized as replacements for diseased or damaged natural ocular lenses. In most cases, an intraocular lens is implanted within an eye at the time of surgically removing the diseased or damaged natural lens, such as for example, in the case of cataracts. For decades, the preferred material for fabricating such intraocular lens implants was poly(methyl methacrylate), which is a rigid, glassy polymer.

Softer, more flexible IOL implants have gained in popularity in more recent years due to their ability to be compressed, folded, rolled or otherwise deformed. Such softer IOL implants may be deformed prior to insertion thereof through an incision in the cornea of an eye. Following insertion of the IOL in an eye, the IOL returns to its original pre-deformed shape due to the memory characteristics of the soft material. Softer, more flexible IOL implants as just described may be implanted into an eye through an incision that is much smaller, i.e., less than 4.0 mm, than that necessary for more rigid IOLs, i.e., 5.5 to 7.0 mm. A larger incision is necessary for more rigid IOL implants because the lens must be inserted through an incision in the cornea slightly larger than the diameter of the inflexible IOL optic portion. Accordingly, more rigid IOL implants have become less popular in the market since larger incisions have been found to be associated with an increased incidence of postoperative complications, such as induced astigmatism.

With recent advances in small-incision cataract surgery, increased emphasis has been placed on developing soft, foldable materials suitable for use in artificial IOL implants. Mazzocco, U.S. Pat. No. 4,573,998, discloses a deformable intraocular lens that can be rolled, folded or stretched to fit through a relatively small incision. The deformable lens is inserted while it is held in its distorted configuration, then released inside the chamber of the eye, whereupon the elastic property of the lens causes it to resume its molded shape. As suitable materials for the deformable lens, Mazzocco discloses polyurethane elastomers, silicone elastomers, hydrogel polymer compounds, organic or synthetic gel compounds and combinations thereof.

In recent years, blue light (400-500 nm) has been recognized as being potentially hazardous to the retina. Accordingly, yellow dyes to block blue light have been used in foldable intraocular lenses, in conjunction with ultraviolet light absorbers, to avoid potential damaging effects. Freeman et al., U.S. Pat. No. 6,353,069, disclose high refractive index copolymers comprising two or more acrylate and/or methacrylate monomers with aromatic groups. Ophthalmic devices made of the copolymers may also include colored dyes, such as the yellow dyes disclosed in U.S. Pat. No. 5,470,932. Such materials exhibit sufficient strength to allow devices made of them, such as intraocular lenses, to be folded or manipulated without fracturing.

Because of intense light absorption in the ultraviolet (UV) and blue light ranges for IOL materials containing blue light and UV light absorbers, it is difficult to cure the IOL materials using traditional photo initiators. Most photo initiators are inactive above 450 nm. Accordingly, IOL materials having blue light absorbers are generally fabricated by thermal cure. Thermal cure is generally more time consuming and thereby less economical than light curing of IOL materials. In addition, precision may not be easily achieved if plastic molds are used in molding the lenses due to deformation of the molds during thermal cure.

SUMMARY OF THE INVENTION

Soft, foldable, high refractive index, intraocular lenses (IOLs) capable of absorbing blue light and ultraviolet (UV) light are prepared in accordance with the present invention through a curing process using visible light photo initiators having suitable absorption above 500 nm to enable curing using a visible light source. The blue light and UV light absorbing IOLs produced in accordance with the present invention protect an eye's retina from potentially damaging blue light and UV light, thereby possibly providing protection from macular degeneration.

Blue light and UV light absorbing IOLs of the present invention are manufactured from materials having ethylenically unsaturated groups such as acrylates, methacrylates, and the like. Suitable materials also include one or more high refractive index monomers, one or more blue light absorbing moieties, one or more UV light absorbing moieties, and one or more photo initiators having suitable absorption above 500 nm.

Accordingly, it is an object of the present invention to provide a process for the production of IOLs with blue light absorption properties.

Another object of the present invention is to provide a process for the production of IOLs having relatively high refractive indices and good clarity.

Another object of the present invention is to provide a process for the production of IOLs that are flexible.

Still another object of the present invention is to provide biocompatible IOLs with blue light absorption properties.

These and other objectives and advantages of the present invention, some of which are specifically described and others that are not, will become apparent from the detailed description and claims that follow.

DETAILED DESCRIPTION OF THE INVENTION

Figure 1:
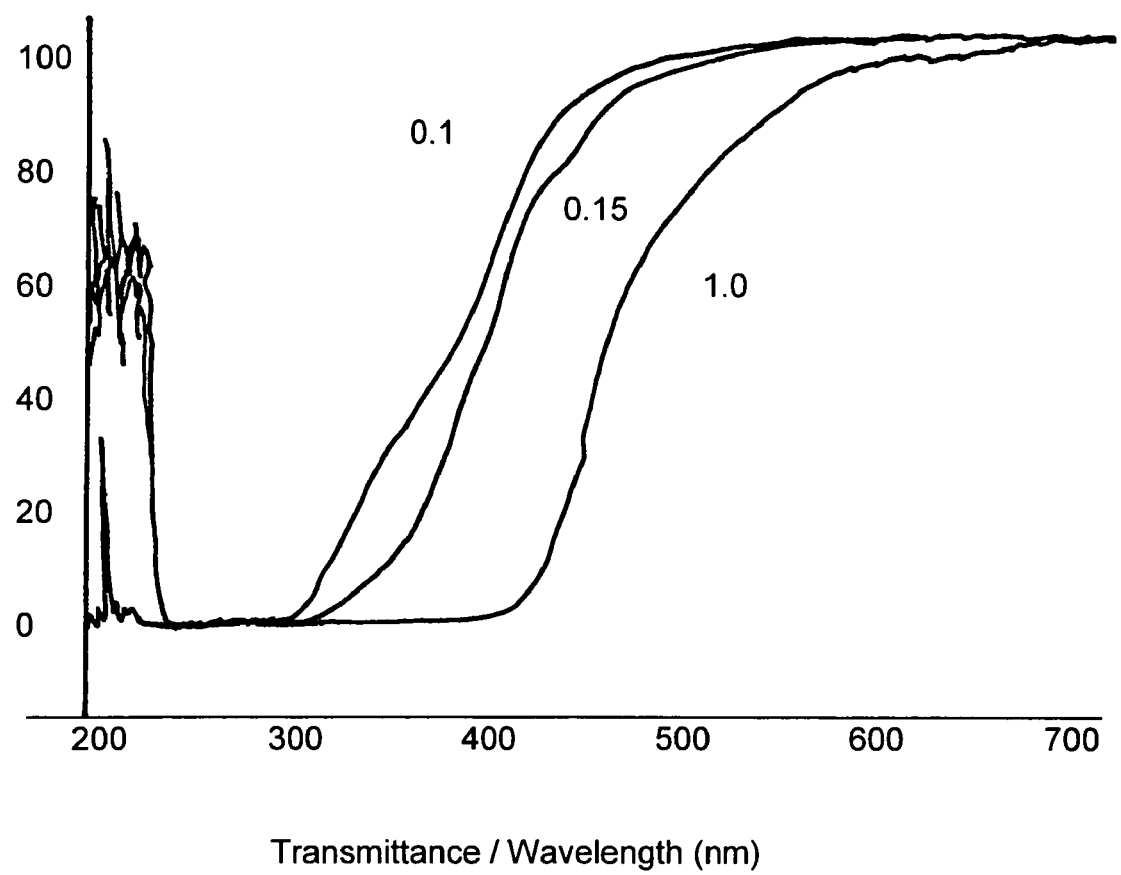
FIG. 1 shows a sample ultraviolet-visible (UV-VIS) spectrum of photo initiator Irgacure-784™ (Ciba Specialty Chemical, Hawthorne, N.Y.) 0.1% in methanol solvent.

The present invention relates to a novel process for the production of high refractive index IOLs with blue light absorption properties to block blue light from reaching the retina of an eye implanted with the IOL. The subject process produces IOLs having blue light and UV light absorption capabilities through a photo curing process. The IOL materials of the present invention include visible light photo initiators having suitable absorption above 500 nm to enable curing in a relatively short period of time, preferably less than several hours, using a visible light source, such as for example a xenon lamp. The blue light and UV light absorbing IOLs produced in accordance with the present invention protect an eye's retina from potentially damaging blue light and UV light, thereby possibly providing protection from macular degeneration.

IOLs of the present invention are produced from one or more monomers and/or prepolymers having ethylenically unsaturated groups such as acrylates, methacrylates, and the like.

Suitable IOL materials in accordance with the present invention also include one or more monomers or prepolymers having a high refractive index. Suitable monomers having a high refractive index include for example but are not limited to those containing various aromatic moieties. Examples of high refractive index monomers include but are not limited to 2-ethylphenoxy methacrylate, 2-ethylphenoxy acrylate, 2-ethylthiophenyl methacrylate, 2-ethylthiophenyl acrylate, 2-ethylaminophenyl methacrylate, 2-ethylaminophenyl acrylate, phenyl methacrylate, benzyl methacrylate, 2-phenylethyl methacrylate, 3-phenylpropyl methacrylate, 4-phenylbutyl methacrylate, 4-methylphenyl methacrylate, 4-methylbenzyl methacrylate, 2,2-methylphenylethyl methacrylate, 2,3-methylphenylethyl methacrylate, 2,4-methylphenylethyl methacrylate, 2-(4-propylphenyl) ethyl methacrylate, 2-(4-(1-methylethyl)phenyl)ethyl methacrylate, 2-(4-methoxyphenyl)ethyl methacrylate, 2-(4-cyclohexylphenyl)ethyl methacrylate, 2-(2-chlorophenyl)ethyl methacrylate, 2-(3-chlorophenyl)ethyl methacrylate, 2-(4-chlorophenyl)ethyl methacrylate, 2-(4-bromophenyl)ethyl methacrylate, 2-(3-phenylphenyl)ethyl methacrylate, 2-(4-phenylphenyl)ethyl methacrylate, 2-(4-benzylphenyl)ethyl methacrylate, and the like.

Suitable high refractive index prepolymers for use in accordance with the present invention include for example but are not limited to acrylate-capped prepolymers of polysiloxanes and methacrylate-capped prepolymers of polysiloxanes, wherein the prepolymers have a suitable number of aromatic moieties so that the refractive index of the prepolymers are at least 1.42. Preferably, each polysiloxane unit of the prepolymer may have an average molecular weight of approximately 1,000 to 10,000 with the prepolymer molecular weight being higher than approximately 1,000, but lower than approximately 300,000.

Suitable IOL materials in accordance with the present invention also include blue light absorbing moieties. Typical blue light absorbing moieties are reactive yellow dyes such as azo-based yellow dye. Examples of such blue light absorbing moieties are provided by but are not limited to those disclosed in D. L. Jinkerson, U.S. Pat. No. 5,662,707, incorporated herein in its entirety by reference, as well as those disclosed in its corresponding co-pending patent applications.

Suitable IOL materials in accordance with the present invention also include UV light absorbing moieties. Suitable ultraviolet light absorbers include for example but are not limited to β-(4-benzotriazoyl-3-hydroxyphenoxy) ethyl acrylate, 4-(2-acryloxyethoxy)-2-hydroxybenzophenone, 4-methacryloxy-2-hydroxybenzophenone, 2-(2'-methacryloxy-5'-methylphenyl)benzotriazole, 2-(2'-hydroxy-5'-methacryoxyethylphenyl)-2H-benzotriazole, 2-[3'-tert-butyl-2'-hydroxy-5'-(3"-methacryloyloxypropyl)phenyl]-5-chlorobenzotriazole, 2-[3'-tert-butyl-5'-(3'-dimethylvinylsilylpropoxy)-2'-hydroxyphenyl]-5-methoxybenzotriazole and 2-[3'-tert-butyl-2'-hydroxy-5'-(3"-methacryloyloxypropoxy)phenyl]-5-chlorobenzotriazole.

Suitable IOL materials in accordance with the present invention also include photointitiators having a suitable-absorption above 500 nm. Examples of suitable photo intiators include but are not limited to substituted UV photo initiators, conjugated ketones, triazine-yl derivatives, metal salts and the like. One particular preferred class of photo intiator for use in the present invention is titanocene derivatives which can be directly photolyzed upon exposure to a light source. An example of such a titanocene derivative is Irgacure-784™ (Ciba Specialty Chemical, Hawthorne, N.Y.), the UV-VIS spectrum of which is illustrated in FIG. 1. Irgacure-784 is a fluorinated diphenyl titanocene having the structure illustrated in Formula 1 below.

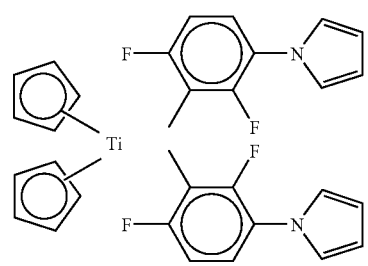

FORMULA 1

To be efficient in visible light polymerization of formulations containing yellow dye, the light source should have sufficient wattage and sufficient emission of light above 450 mn. The preferred light source for use in accordance with the present invention is a high intensity Xenon lamp, such as for example but not limited to Lamp Model RC-257, a pulsed lamp, available commercially from Xenon Corporation, Woburn, Mass. Lamp Model RC-257 provides sufficient wattage and sufficient emission of light above 450 mn for efficient polymerization of formulations containing yellow dye. Using such a high intensity Xenon lamp allows for curing to be completed in less than 4 hours, preferably less than one hour, even more preferably in less than 30 minutes, depending on the intensity applied.

The process of the present invention for preparing flexible, high refractive index IOLs with blue light and UV light absorption capability is described in still greater detail in the examples provided below.

EXAMPLE 1

Synthesis of N,N-bis-(2-hydroxyethyl)-(4-phenylazo) aniline, (Solvent Yellow 58)

The synthesis of N,N-bis-(2-hydroxyethyl)-(4-phenylazo) aniline is accomplished by the coupling of a diazonium salt of aniline with N-phenyl diethanolamine. A detailed procedure for synthesizing N,N-bis-(2-hydroxyethyl)-(4-phenylazo) aniline is disclosed in D. L. Jinkerson, U.S. Pat. No. 5,470,932.

EXAMPLE 2

Synthesis of N,N-bis-(2-[acryloxyethyl)-(4'-phenylazo)aniline

A 1000 mL 3-neck, round bottom flask connected with a reflux condenser and a drying tube, is charged with 250 mL of methylene chloride, 5.7 grams (0.02 mole) of N,N-bis-(2-hydroxyethyl)-(4-phenylazo)aniline aniline and 4.04 grams of triethylamine. The contents are chilled using an ice bath. Through a dropping funnel, 7.24 g (0.04 mole) of acryloyl chloride is added into the flask over a period of 30 minutes. The ice bath is then removed and the contents are continuously stirred overnight. The mixture is then filtered and then condensed using a rotavapor. High performance liquid chromatography (HPLC) analysis indicates only one major product. The product is then passed through silica gel chromatography to give final purified product with a yield of at least 80 percent. The product is identified by nuclear magnetic resonance (NMR) and Mass Spectroscopy.

EXAMPLE 3

Preparation of Hydroxybutyl-Terminated Copolymer of Dimethylsiloxane and Diphenylsiloxane (with 25 mole Percent Phenyl Content)

1,3-bis(hydroxybutyl)tetramethyl disiloxane (33.70 g, 0.118 mole), dimethyidimethoxysilane (403.18 g, 3.25 moles) and diphenyldimethoxysilane (272.33 g, 1.08 moles) were added in a one-liter round bottom flask. Water (78.29 g) and concentrated hydrochloric acid (11.9 mL) were then slowly added to the flask. The contents of the flask were refluxed for one hour. Methanol (253.3 mL) was distilled from the contents. Water (160 mL) and concentrated hydrochloric acid (130 mL) was added to the flask. The contents of the flask were refluxed for one hour. The contents of the flask were then poured into a separatory funnel. The silicone layer was separated, diluted with 500 mL ether and washed once with 250 mL water, twice with 250 mL 5-percent sodium bicarbonate aqueous solution and twice with 250 mL water. The final organic layer was dried with magnesium sulfate, and then vacuum stripped at 80 degrees Celsius (0.1 mm Hg) to give the crude product. The crude product was then dissolved in 50/50 cyclohexane/methylene chloride and then passed through a silica gel column with the same solvent mixture. The final product was collected in tetrahydrofuran (THF) by passing THF through the silica gel column. The THF fractions were combined, dried and vacuum stripped to give the final product. Size Exclusion Chromatography (SEC) measurements of the final product indicated less than three percent cyclics and a molecular weight of 2821 by titration.

EXAMPLE 4

Preparation of Methacylate-Capped Prepolymer of Polysiloxane Containing Both Dimethylsiloxane and Diphenylsiloxane Units A 500-mL round bottom flask equipped with reflux condenser and nitrogen blanket was charged with isophorone diisocyanate (5.031 g, 0.0227 mole), the hydroxybutyl-terminated copolymer of dimethylsiloxane and the diphenylsiloxane from Example 3 (51.4465 g, 0.0189 mole), dibutyltin dilaurate (0.1811 g) and methylene chloride (150 mL). The flask contents were refluxed. After about 90 hours of reflux, the isocyanate was found decreased to 16.2 percent (theoretical 16.7 percent) of original. The contents of the flask were allowed to cool to ambient temperature. HEMA (1.1572 g) and 1,1'-2-bi-naphthol (5.7 mg) were added to the flask and stirred. After seven days, NCO peak disappeared from IR spectrum and the reaction was terminated. The product was obtained at quantitative yield after removing solvent.

EXAMPLE 5

Preparation of High Refractive Index Hydrogels Containing a Yellow Dye Moiety and UV Absorber Useful for IOL Application A formulation consists of 50 parts of prepolymer of Example 5, 20 parts of benzyl acrylate, 10 parts of benzyl methacrylate, 20 parts of N,N-dimethyl acrylamide, 0.25 parts benzotriazole methacrylate, 0.2 part N,N-bis-(2-[acryloxyethyl)-(4'-phenylazo)aniline as described in Example 2,and 1 part of Irgacure-784. The mix is cured between two silane-treated glass plates under a high intensity visible light lamp, Model RC-257 (Xenon Corporation) for 1 hour. The cured films are then released, extracted in isopropanol for over 4 hours and dried in a vacuum oven at 70 degrees Celsius overnight. The dried films are then placed in a borate buffered saline overnight before characterization. The films have a thickness of 170-200 microns. The UV-VIS absorption of hydrogel films are then measured and have less than 1% transmittance below 400 nm and less than 60% transmittance but above 40%, below 450 nm. Mechanical properties of the processed films can be adjusted by adjustment of the light intensity applied for curing.

Soft, foldable, relatively high refractive index of approximately 1.42 or greater, relatively high elongation of approximately 100 percent or greater, IOLs with blue light absorption properties are synthesized through the process of the present invention. The IOLs produced as described herein have the flexibility required to allow the same to be folded or deformed for insertion into an eye through the smallest possible surgical incision, i.e., 3.5 mm or smaller. It is unexpected that the subject IOLs described herein could possess the ideal physical properties disclosed herein. The ideal physical properties of the subject IOLs are unexpected due to difficulties previously associated with photo curing of blue light absorbing and UV light absorbing materials.

IOLs manufactured using the process of the present invention can be of any design capable of being rolled or folded for implantation through a relatively small surgical incision, i.e., 3.5 mm or less. Such IOLs may be manufactured to have an optic portion and haptic portions made of the same or differing materials. Once the material(s) are selected, the same may be cast in molds of the desired shape, cured and removed from the molds. After such molding, the IOLs are treated in accordance with the process of the present invention and then cleaned, polished, packaged and sterilized by customary methods known to those skilled in the art. Alternatively, the materials may be cast in rods, cut into disks and lathed into the desired shape as known to those skilled in the art.

In addition to IOLs, the process of the present invention is also suitable for use in the production of other medical or ophthalmic devices such as contact lenses, keratoprostheses, capsular bag extension rings, corneal inlays, corneal rings and like devices.

IOLs manufactured using the process of the present invention are used as customary in the field of ophthalmology. For example, in a surgical cataract procedure, an incision is placed in the cornea of an eye. Through the corneal incision the cataractous natural lens of the eye is removed (aphakic application) and an IOL is inserted into the anterior chamber, posterior chamber or lens capsule of the eye prior to closing the incision. However, the subject ophthalmic devices may likewise be used in accordance with other surgical procedures known to those skilled in the field of ophthalmology.

While there is shown and described herein a process for producing IOLs with blue light and ultraviolet light absorption capabilities, it will be manifest to those skilled in the art that various modifications may be made without departing from the spirit and scope of the underlying inventive concept and that the same is not limited to particular processes and structures herein shown and described except insofar as indicated by the scope of the appended claims.

We claim:

1. A method for manufacturing medical devices comprising:
   providing a polymer composition comprising one or more monomers or prepolymers, one or more blue light absorption compounds and one or more ultraviolet light absorption compounds, and one or more photo initiators that can absorb light above 500 nm; and
   exposing said polymer composition to visible light for less than about 4 hours.

2. A method for manufacturing medical devices comprising:
   providing a polymer composition comprising one or more monomers or prepolymers selected from the group consisting of 2-phenylethyl methacrylate, methacrylate-capped prepolymers of polysiloxanes and acrylate-capped prepolymers of polysiloxanes having a suitable number of aromatic moieties to provide the medical device with a refractive index of at least 1.42, one or more blue light absorption compounds and one or more ultraviolet light absorption compounds, and one or more photo initiators that can absorb light above 500 nm; and
   exposing said polymer composition to visible light for less than about 4 hours.

3. The method of claim 1 or 2 wherein said medical device is selected from the group consisting of contact lenses, keratoprostheses, capsular bag extension rings, corneal inlays and corneal rings.

4. The method of claim 1 or 2 wherein said medical device is an intraocular lens.

5. The method of claim 1 or 2 wherein said blue light absorption moieties are one or more reactive yellow dyes.

6. The method of claim 1 or 2 wherein said blue light absorption moieties are one or more azo-based yellow dyes.

7. The method of claim 1 wherein the one or more monomers or prepolymers is an acrylate or methacrylate material.

8. The method of claim 1 wherein said wherein said one or more monomers is selected from the group consisting of 2-ethylphenoxy methacrylate, 2-ethylphenoxy acrylate, 2-ethylthiophenyl methacrylate, 2-ethylthiophenyl acrylate, 2-ethylaminophenyl methacrylate, 2-ethylaminophenyl acrylate, phenyl methacrylate, benzyl methacrylate, 2-phenylethyl methacrylate, 3-phenylpropyl methacrylate, 4-phenylbutyl methacrylate, 4-methylphenyl methacrylate, 4-methylbenzyl methacrylate, 2,2-methylphenylethyl methacrylate, 2,3-methylphenylethyl methacrylate, 2,4-methylphenylethyl methacrylate, 2-(4-propylphenyl)ethyl methacrylate, 2-(4-(1 -methylethyl)phenyl)ethyl methacrylate, 2-(4-methoxyphenyl)ethyl methacrylate, 2-(4-cyclohexylphenyl)ethyl methacrylate, 2-(2-chlorophenyl)ethyl methacrylate, 2-(3-chlorophenyl)ethyl methacrylate, 2-(4-chlorophenyl)ethyl methacrylate, 2-(4-bromophenyl)ethyl methacrylate, 2-(3-phenylphenyl)ethyl methacrylate, 2-(4-phenylphenyl)ethyl methacrylate and 2-(4-benzylphenyl) ethyl methacrylate.

9. The method of claim 1 the one or more prepolymers is selected from the group consisting of methacrylate-capped prepolymers of polysiloxanes and acrylate-capped prepolymers of polysiloxanes having a suitable number of aromatic moieties to provide a prepolymer with a refractive index of at least 1.42.

10. The method of claim 1 or 2 wherein said ultraviolet light absorption compounds benzotriazole compounds.

11. The method of claim 1 or 2 wherein said ultraviolet light absorption compounds are selected from the group consisting of β-(4-benzotriazoyl-3-hydroxyphenoxy) ethyl acrylate, 4-(2-acryloxyethoxy)-2-hydroxybenzophenone, 4-methacryloxy-2-hydroxybenzophenone, 2-(2'-methacryloxy-5'-methylphenyl)benzotriazole, 2-(2'-hydroxy-5'-methacryoxyethylphenyl)-2H-benzotriazole, 2-[3'-tert-butyl-2'-hydroxy-5'-(3"-methacryloyloxypropyl)phenyl]-5-chlorobenzotriazole, 2-[3'-tert-butyl-5'-(3"-dimethylvinylsilylpropoxy)-2'-hydroxyphenyl]-5-methoxybenzotriazole and 2-[3'-tert-butyl-2'-hydroxy-5'-(3"-methacryloyloxypropoxy)phenyl]-5-chlorobenzotriazole.

12. The method of claim 1 or 2 wherein said photo initiators are selected from the group consisting of conjugated ketones, triazine-yl derivatives and metal salts.

13. The method of claim 1 or 2 wherein said photo initiators are titanocene derivatives.

14. The method of claim 1 or 2, wherein said step of exposing is carried out for about 2 hours or less.

15. A method for manufacturing an intraocular lens comprising:
   providing a polymer composition comprising one or more monomers or prepolymers selected from the group consisting of 2-phenylethyl methacrylate, 2-ethylphenoxy methacrylate, 2-ethylphenoxy acrylate, methacrylate-capped prepolymers of polysiloxanes and acrylate-capped prepolymers of polysiloxanes having a suitable number of aromatic moieties to provide the intraocular lens with a refractive index of at least 1.42, an azo-based yellow dye and one or more ultraviolet light absorption compounds, and one or more photo initiators that can absorb light above 500 nm; and
   exposing said polymer composition to visible light for less than about 4 hours.

16. The method of claim 15 wherein said ultraviolet light absorption compounds are selected from the group consisting of β-(4-benzotriazoyl-3-hydroxyphenoxy) ethyl acrylate, 4-(2-acryloxyethoxy)-2-hydroxybenzophenone, 4-methacryloxy-2-hydroxybenzophenone, 2-(2 '-methacryloxy-5'-methylphenyl)benzotriazole, 2-(2'-hydroxy-5'-methacryoxyethylphenyl)-2H-benzotriazole, 2-[3'-tert-butyl-2'-hydroxy-5'-(3"-methacryloyloxypropyl)phenyl]-5-chlorobenzotriazole, 2-[3'-tert-butyl-5'-(3"-dimethylvinylsilylpropoxy)-2'-hydroxyphenyl]-5-methoxybenzotriazole and 2-[3'-tert-butyl-2'-hydroxy-5'-(3"-methacryloyloxypropoxy)phenyl]-5-chlorobenzotriazole.

17. The method of claim 15 wherein said photo initiators are selected from the group consisting of conjugated ketones, triazine-yl derivatives and a fluorinated diphenyl titanocene derivative.

18. The method of claim 15 wherein said photo initiator is a fluorinated diphenyl titanocene derivative.

* * * * *